United States Patent
Kumar

(10) Patent No.: US 6,547,562 B2
(45) Date of Patent: Apr. 15, 2003

(54) PSEUDO-ETCHING OF DIAMOND-LIKE CARBON COATED INSTRUMENTS

(75) Inventor: Ajay Kumar, Palmdale, CA (US)

(73) Assignee: Nobel Biocare AB, Gothenburg (SE)

( * ) Notice: Subject to any disclaimer, the term of this patent is extended or adjusted under 35 U.S.C. 154(b) by 0 days.

(21) Appl. No.: 09/853,256

(22) Filed: May 11, 2001

(65) Prior Publication Data

US 2002/0028422 A1 Mar. 7, 2002

Related U.S. Application Data

(60) Provisional application No. 60/203,212, filed on May 11, 2000.

(51) Int. Cl.$^7$ ................................................ A61C 3/02
(52) U.S. Cl. ........................ 433/165; 606/80; 427/2.28; 427/2.29
(58) Field of Search ........................... 433/165; 606/80, 606/72; 427/2.1, 2.28, 2.29

(56) References Cited

U.S. PATENT DOCUMENTS

| | | |
|---|---|---|
| 3,971,135 A | 7/1976 | Leu |
| 4,504,519 A | 3/1985 | Zelez ............................ 427/39 |
| 4,560,308 A | 12/1985 | Deller ............................ 407/53 |
| 4,681,541 A | 7/1987 | Snaper .......................... 433/165 |
| 4,787,848 A | 11/1988 | Ross ............................. 433/165 |
| 4,820,156 A | 4/1989 | Ross ............................. 433/165 |
| 4,855,026 A | 8/1989 | Sioshansi ................. 204/192.11 |
| 4,859,493 A | 8/1989 | Lemelson .................... 427/45.1 |
| 4,943,236 A | 7/1990 | Linkow et al. ............... 433/165 |
| 4,960,643 A | 10/1990 | Lemelson .................... 428/408 |
| 4,987,007 A | 1/1991 | Wagal et al. ................. 427/53.1 |
| 5,078,605 A | 1/1992 | Sutter et al. ................. 433/165 |
| 5,085,586 A | 2/1992 | Johnson ...................... 433/224 |
| 5,096,352 A | 3/1992 | Lemelson .................... 411/424 |
| 5,096,418 A | 3/1992 | Coss ............................ 433/29 |
| 5,098,737 A | 3/1992 | Collins et al. ................ 427/53.1 |
| 5,203,804 A | 4/1993 | Nikutowski et al. ............. 433/8 |
| 5,261,818 A | 11/1993 | Shaw ........................... 433/165 |
| 5,299,937 A | 4/1994 | Gow ............................ 433/165 |
| 5,538,423 A | 7/1996 | Coss et al. ..................... 433/27 |
| 5,573,684 A | 11/1996 | Winston et al. .......... 219/121.85 |
| 5,575,650 A | 11/1996 | Niznick et al. .............. 433/165 |
| 5,653,812 A | 8/1997 | Petrmichl et al. .......... 118/723 E |
| 5,681,653 A | 10/1997 | Hammond et al. .......... 428/336 |
| 5,725,573 A | 3/1998 | Dearnaley et al. .............. 623/2 |
| 5,731,045 A | 3/1998 | Dearnaley et al. ........... 427/527 |
| 5,741,267 A | 4/1998 | Jorneus et al. .............. 606/102 |
| 5,747,120 A | 5/1998 | McLean, II et al. ......... 427/596 |
| 5,763,072 A | 6/1998 | Kato et al. ................... 428/336 |
| 5,763,087 A | 6/1998 | Falabella ..................... 428/408 |

(List continued on next page.)

FOREIGN PATENT DOCUMENTS

| | | |
|---|---|---|
| GB | 966604 | 8/1964 |
| WO | WO 00/27301 | 5/2000 |

OTHER PUBLICATIONS

U. Bogli, et al. *Smoothening of Diamond Films with an ARF Laser*, Elsevier Science Publishers, pp. 782–788, ©1992.
U.S. patent application Ser. No. 09/439,247, Kumar, filed Nov. 12, 1999.

(List continued on next page.)

Primary Examiner—Cary E. O'Connor
(74) Attorney, Agent, or Firm—Knobbe, Martens, Olson & Bear LLP

(57) ABSTRACT

The invention provides a depth gauging system and a method for forming depth indicating bands on amorphous hard carbon coated dental tool bits and the like. The method uses a laser to process, treat or pseudo-etch selected surfaces of the coated tool bit. Advantageously, the laser pseudo-etching creates bands or indicia that substantially preserve or retain some or all of the desirable bulk properties of the hard carbon coating, for example, the corrosion resistance. Desirably, the bands provide visual differentiation during the preparation of an osteotomy in bone material which allows a surgeon to precisely control the depth of the osteotomy.

107 Claims, 6 Drawing Sheets

U.S. PATENT DOCUMENTS

| | | | |
|---|---|---|---|
| 5,763,879 A | 6/1998 | Zimmer et al. | 208/306 |
| 5,766,394 A | 6/1998 | Anderson et al. | 156/89.11 |
| 5,772,760 A | 6/1998 | Gruen et al. | 117/104 |
| 5,785,522 A | 7/1998 | Bergstrom et al. | 433/72 |
| 5,792,256 A | 8/1998 | Kucherov et al. | 117/89 |
| 5,799,549 A | 9/1998 | Decker et al. | 76/104.1 |
| 5,839,897 A | 11/1998 | Bordes | 433/165 |
| 5,868,572 A | 2/1999 | Lazzara et al. | 433/173 |
| 5,941,706 A * | 8/1999 | Ura | 433/165 |
| 5,997,298 A | 12/1999 | Nowak | 433/165 |
| 6,022,350 A | 2/2000 | Ganem | 606/61 |

OTHER PUBLICATIONS

"Super–Slick", *Mechanical Engineering*, John DeGaspari, pp. 46–48, Apr. 1999.

"Diamond Coated Total Hip Replacements", *Clinical Orthopedics and Related Research*, Reijo Lappalainen, Asko Anttila and Harri Heinonen, No. 352, pp. 118–124, Jul. 1998.

"Development and Status of Diamondlike Carbon", *Synthetic Diamond: Emerging CVD Science and Technology*, A Wiley–Interscience Publication, Alfred Grill and Bernard S. Meyerson, pp. 91–96, 110–112, 121, 134–135, ©1994.

"Deposition of diamond–like carbon", *Thin Film Diamond*, Chapman & Hall, J. Robertson, pp. 107–109, ©1994.

"Atomic and Crystal Structures of Diamond", *Diamond Chemical Vapor Deposition*, Noyes Publications, Huimin Liu and David S. Dandy, pp. 8–9, ©1995.

"Raman Spectroscopy of Amorphous Carbon", *Covalently Bonded Disordered Thin–Film Materials*, Materials Research Society, Symposium proceedings vol. 498, D.R. Tallant, T.A. Friedmann, N.A. Missert, M.P. Siegal and J.P. Sullivan, p. 37, Dec. 2–4, 1997.

* cited by examiner

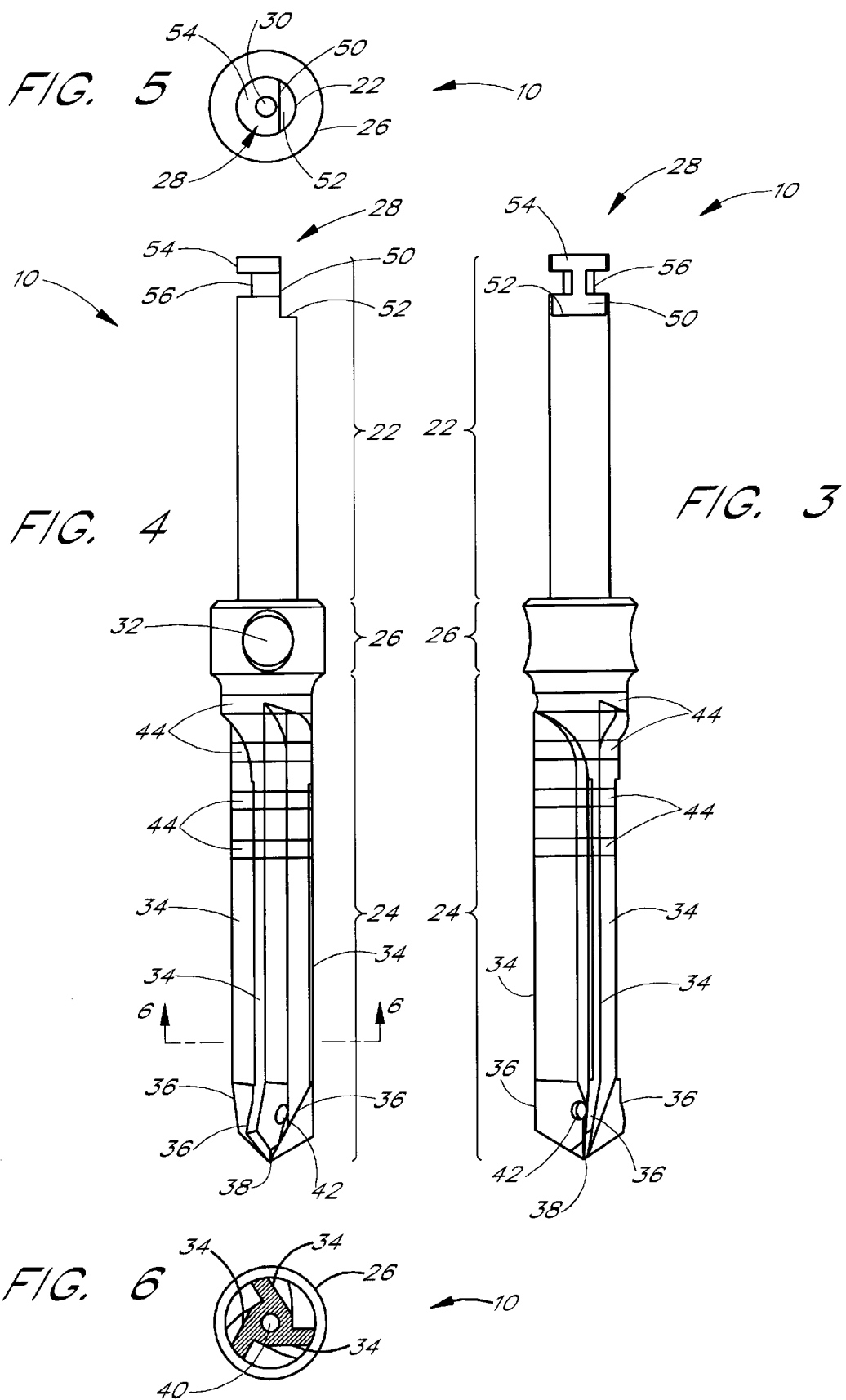

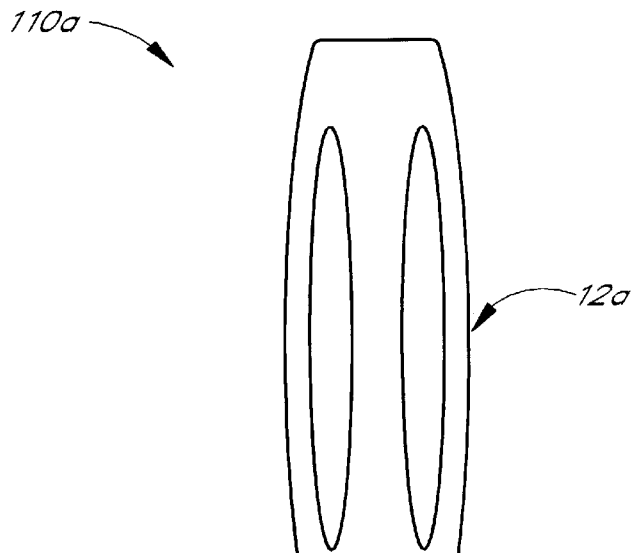
FIG. 9
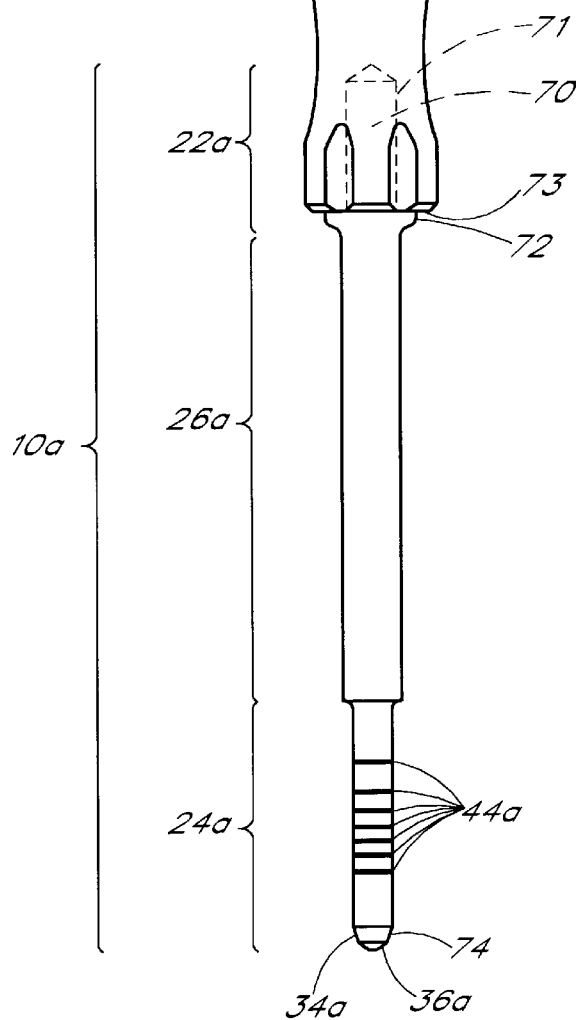
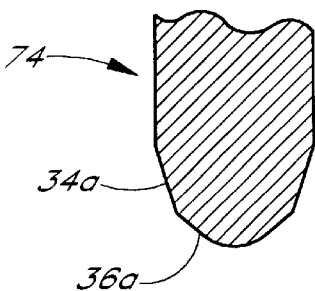
FIG. 10

PSEUDO-ETCHING OF DIAMOND-LIKE CARBON COATED INSTRUMENTS

RELATED APPLICATIONS

This application claims the benefit of U.S. Provisional Application No. 60/203,212, filed May 11, 2000, the entire disclosure of which is hereby incorporated by reference herein.

BACKGROUND OF THE INVENTION

1. Field of the Invention

The present invention relates generally to surgical instruments and, more particularly, to surgical drilling bits and the like and, most particularly, to pseudo-etching of depth indicating bands and/or other identifying markings or indicia on diamond-like carbon coated dental drilling bits and the like used to prepare an osteotomy in the jawbone of a patient.

2. Description of the Related Art

Dental implants are surgically implanted in a patient's jawbone to provide anchors for prosthetic devices such as artificial teeth, crowns, bridges, dentures and the like. Dental implants allow people who lose their teeth to be able to comfortably smile, speak, and chew.

Typically, the dental implant that is implanted in the bone of a patient's jaw supports a socket. This socket is accessible through the overlying gum tissue for receiving and supporting one or more dental attachments or components. In turn, these components are useful to support the prosthodontic restoration.

The first step for installing an implant usually involves making an incision in the patient's gum or gingiva. Next, typically, a hole or osteotomy is formed in the jawbone of the patient. This may involve widening of a pre-existing cavity or the formation of a fresh one. The implant is then fixtured into the osteotomy. More than one osteotomy may be prepared to support a plurality of implants. Once the implant is properly secured in its subgingival position in the osteotomy a healing screw is threaded tightly over the implant.

This is followed by a healing period in which the bone is allowed to grow and surround and retain the implant. This process is called "osseointegration." The gum tissue is also allowed to heal over the implant and the healing screw. For implants in the mandible (lower jaw), healing typically requires about three months; for implants in the maxilla (upper jaw), the healing period is usually about six months.

After the osseointegration occurs and the gum has healed, the gum is reopened by making an incision in it and the healing screw is removed. A suitable healing abutment is attached to the implant. A second healing period ensues in which the gum tissue is allowed to heal around the healing abutment. Typically, this second healing period lasts from four to eight weeks.

After the second healing period, the healing abutment is removed from the implant. Typically, an impression is taken of the patient's mouth to fabricate a prosthesis or dental restoration. An abutment which supports the final restoration is attached to the implant. Lastly, the restoration is cemented or screwed to the abutment and/or implant to complete the placement of the prosthodontic restoration in the patient's mouth.

The step of forming an osteotomy typically involves drilling a hole in the patient's jawbone, utilizing one or more suitable drilling bits. This can be a difficult procedure and can cause discomfort and trauma for the patient, at least partially, due to the pain and shock involved with the penetration of a relatively large drilling bit in a person's jawbone. Drilling in high bone densities can further exacerbate and complicate the osteotomy preparation.

The high rotational drilling speeds typically involved can also generate a significant amount of heat. This is especially true since the osteotomy is not a through hole. Disadvantageously, the large amounts of heat can cause bone "necrosis" due to burning. Again, this adds to the trauma and suffering of the patient, and can inhibit the desired healing of the bone and osseointegration of the implant.

The high rotational drilling speeds can also result in high frictional forces and torques between the bone and the drilling bit. Undesirably, this increases the risk of bone fracture, and again this is detrimental to the patient. Moreover, the high frictional forces and torques may cause breakage of the drilling bit. Disadvantageously, this further complicates the procedure and adds to the trauma of the patient.

In some cases, dental counterbores are utilized to countersink the osteotomy for receiving a particularly configured implant. Also, dental threadformers may be used to thread the osteotomy for receiving a threaded implant. Both counterbores and threadformers involve removal of bone material and can cause some or all of the above-mentioned disadvantages.

In some instances, an osteotome is used to form an osteotomy in soft bone. An osteotome typically has a cutting tip that is manually manipulated by the dental practitioner to cut/compress the soft bony material. Again, the use of conventional osteotomes can suffer from some or all of the above-mentioned disadvantages.

As indicated above, it can be difficult to perform osteotomy preparing procedures efficiently, and without causing significant discomfort and trauma to the patient. Moreover, the drilling bits, counterbores, threadformers, and osteotome cutting tips are exposed to frictional forces and corrosive environments (in the patient's mouth and possibly during sterilization). As a result, in many cases, these instruments have to be replaced frequently since wear and corrosion reduce their effectiveness. Disadvantageously, this also adds to the cost of the implant procedure.

It is also important that the bore-holes or osteotomies be prepared to a suitable depth to ensure proper seating of the dental implant. Care should also be taken when an osteotomy is being prepared in parts of the jaw where a nerve or nerve system is located to prevent damage to the nerves. It can be difficult to provide reliable and durable depth indicators during the preparation of an osteotomy.

SUMMARY OF THE INVENTION

It is one advantage of the invention to provide a depth gauging system and a method for forming depth indicating bands on amorphous hard carbon coated dental tool bits and the like. The method uses a laser to process, treat or pseudo-etch selected surfaces of the coated tool bit. Advantageously, the laser pseudo-etching creates bands or indicia that substantially preserve or retain some or all of the desirable bulk properties of the hard carbon coating, for example, the corrosion resistance. Desirably, the bands provide visual differentiation during the preparation of an osteotomy in bone material which allows a surgeon to precisely and exactly control the depth of the osteotomy.

In accordance with one embodiment, the invention provides a method of treating the surface of a surgical instrument to provide visual differentiation. The method comprises the step of providing the instrument comprising a cutting head and a mounting shank adapted to engage a handpiece or handle. A hard carbon coating is formed on the cutting head of the instrument. One or more selected surfaces of the cutting head are pseudo-etched to provide one or more bands having a predetermined spacing for indicating the depth of an osteotomy.

In accordance with another embodiment, the invention provides a method of processing the surface of a coated dental cutting instrument to provide visual differentiation. The method comprises the step of providing the instrument comprising a cutting head and a mounting shank adapted to engage a handpiece or handle. An amorphous hard carbon film is formed on at least the cutting head of the instrument. A plurality of selected coated surfaces of the cutting head are laser processed to pseudo-etch a plurality of indicia having a predetermined spacing for precisely indicating the depth of an osteotomy formed in a jawbone.

In accordance with one embodiment, the invention provides a surgical instrument for providing visual differentiation. The instrument generally comprises a main body portion, a coating of amorphous hard carbon applied on at least a portion of the main body portion, and one or more indicia formed on the main body portion. The indicia are formed by laser pseudo-etching of selected surfaces of the hard carbon coated main body portion to provide a depth gauging system on the instrument. Advantageously, the surface finish of the indicia substantially preserves the protective coating properties of amorphous hard carbon.

In accordance with another embodiment, the invention provides a dental drilling system for preparing an osteotomy. The system generally comprises a tool bit, a handpiece for holding the tool bit, a coating on the tool bit in the form of diamond-like carbon (DLC) and a plurality of pseudo-etched bands formed on the coating. The tool bit includes a cutting head for removing bone/tissue material to form an osteotomy. The handpiece is adapted to provide rotational motion to the tool bit. The diamond-like carbon (DLC) coating improves the cutting performance of the tool bit. The bands provide visual differentiation and advantageously are corrosion resistant.

For purposes of summarizing the invention certain aspects, advantages and novel features of the invention have been described herein above. Of course, it is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and some of its features and advantages, certain preferred embodiments and modifications thereof will become apparent to those skilled in the art from the detailed description herein having reference to the figures that follow, of which:

FIG. 3 is a front elevation view of a drilling bit comprising depth indicating bands in accordance with one embodiment of the present invention;

FIG. 4 is a side elevation view of the drilling bit of FIG. 3;

FIG. 5 is a top plan view of the drilling bit of FIG. 3;

FIG. 6 is a sectional view along line 6—6 of FIG. 4;

FIG. 9 is a front elevation view of an osteotome comprising depth indicating bands in accordance with one embodiment of the present invention;

FIG. 10 is an enlarged view of one end of the cutting tip of the osteotome of FIG. 9.

DETAILED DESCRIPTION OF THE PREFERRED EMBODIMENTS

Figure 1:
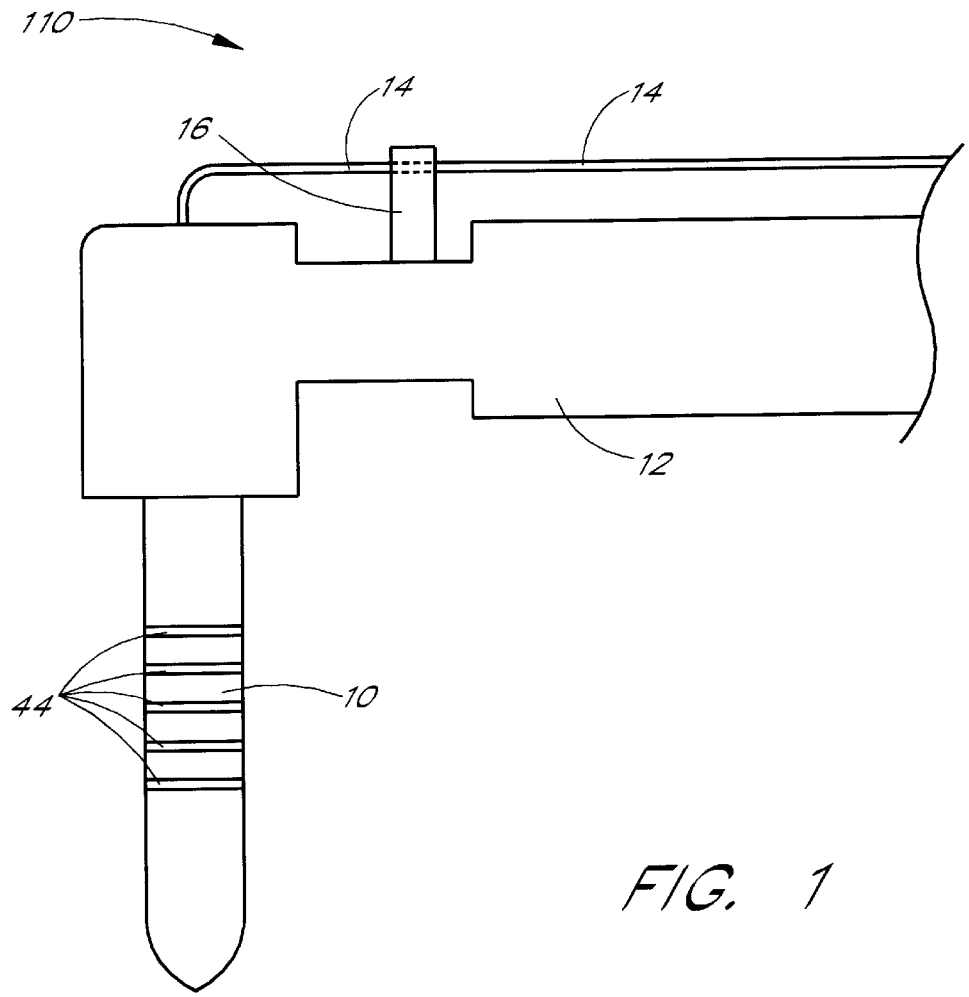
FIG. 1 is a schematic illustration of a dental drilling/cutting system comprising a tool bit having a plurality of depth indicating bands in accordance with one embodiment of the present invention.

FIG. 1 is a schematic illustration of a dental drilling/cutting system or apparatus 110 in accordance with one embodiment. The drilling system 110 generally includes a tool bit or tool 10 connected to a drill or handpiece 12 for providing rotor torque to the tool bit 10. The handpiece 12 may be powered by a wide variety of commercially available power sources, such as pneumatic, hydraulic or electric motors, as is known in the art. Alternatively, the tool bit or surgical instrument 10 may be configured for hand or finger manipulation. The drilling system 110 further includes an irrigation cannula 14. The irrigation cannula 14 is supported by a support member 16 on the handpiece 12. The irrigation cannula 14 is in fluid communication with the tool bit 10 and provides fluid, for washing and cooling, during operation.

Figure 2:
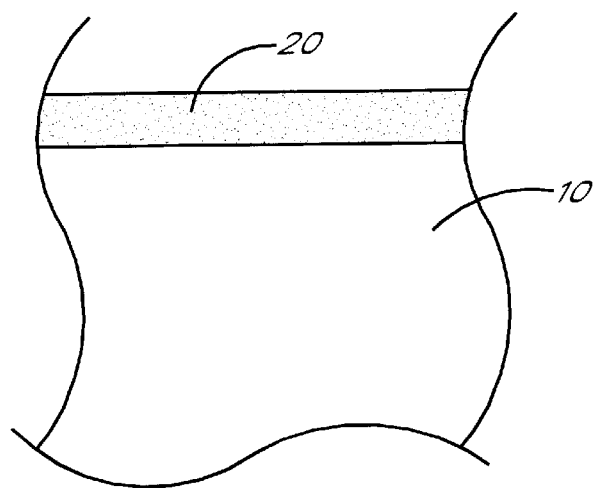
FIG. 2 is a schematic illustration of the coating (not to scale) on the tool bit of FIG. 1.

In one embodiment, at least a portion of the tool bit or dental instrument 10 (FIG. 1) is coated with an amorphous hard carbon coating or film 20, as schematically illustrated in FIG. 2. The coating 20 can comprise, for example, a diamond-like carbon (DLC) coating 20, an amorphous diamond coating 20, a crystalline diamond coating 20, or a combination thereof. The coating 20 can be multi-layered and comprise one or more layers. The term "hard carbon," as used herein, can denote any or all of the above giving due consideration to achieving some or all of the benefits and advantages of the present invention. Some embodiments of diamond-like carbon coated dental instruments are disclosed in U.S. patent application Ser. No. 09/439,247, filed Nov. 12, 1999, the entire disclosure of which is hereby incorporated by reference herein.

As discussed in further detail later herein, in one embodiment, one or more osteotomy depth indicating bands, indicia or markings 44 are provided on the coated tool bit 10. The bands 44 are preferably formed by an etching or pseudo-etching surface treatment and are colored or shaded distinctly or in contrast to the adjacent surface(s) of the tool bit 10. Advantageously, the surface processing of the coated tool bit 10 to form the bands 44 does not adversely affect one or more of the desirable properties, for example, the corrosion resistance, of the coating 20.

In one embodiment, the coating 20 (FIG. 2) is a diamond-like carbon (DLC) coating 20. In another embodiment the coating 20 comprises an amorphous diamond coating 20. Generally, diamond-like carbon (DLC) is hydrogenated and this feature distinguishes it from amorphous diamond which has a smaller or negligible proportion of hydrogen. Both comprise an amorphous arrangement of atoms and a major or substantially sizable proportion of $sp^3$ bonding which results in high mechanical hardness, low friction, chemical inertness, more heat transfer, and other desirable properties. Diamond-like carbon (DLC) and amorphous diamond can also include some degree of $sp^2$ bonding. In general, the "hard carbon" coating 20 of the present invention comprises (a) at least some $sp^3$ bonding, (b) some, negligible or no $sp^2$ bonding, and (c) some, negligible or no hydrogenation. A discussion of $sp^n$ bonding configurations is available in many references, for example, "Synthetic Diamond: Emerging CVD Science and Technology," edited by K. E. Spear and J. P. Dismukes (sponsored by the Electrochemical Society, Inc.), Wiley, N.Y., 1994. Though there are a wide variety of commercially available "hard carbon" coatings, the present invention provides certain novel and unique benefits and advantages over the prior art in the field of oral surgery, and particularly in the field of dental implantology as related to the preparation of an osteotomy in a patient's jawbone.

As discussed in greater detail later herein, one advantage of the coating 20 (FIG. 2) is that it provides a reduced coefficient of friction (enhanced lubriciousness) between the jawbone and the hard carbon coated dental instrument of the present invention, and desirably improves the cutting performance. Some of the other benefits and advantages arise as a consequence of the coating 20 properties of high mechanical hardness (wear resistance), corrosion resistance, and high thermal conductivity. Some or all of these desirable properties of the hard carbon coating 20 translate into reduced discomfort for the patient, reduced chances of accidents, bone fracture and bone necrosis, increased operational ease for the dental surgeon, saving of valuable time, and reduction in the cost of the implant procedure.

In one embodiment, and referring to FIGS. 3 to 6, the tool bit 10 (FIG. 1) is a drilling bit 10 for forming an implant-receiving osteotomy in a patient's jawbone. The drilling bit 10 generally comprises a mounting shank 22 and a cutting head 24 joined by a linking member 26. The mounting shank 22 is generally cylindrical in shape and includes a proximal end or chuck 28 which is sized and configured to be received in handpieces of conventional dental drilling systems, for example, the handpiece 12 of the dental drilling system 110 shown in FIG. 1. The chuck 28 includes a generally I-shaped flat side 50 which defines a step 52 and a generally semi-circular disk 54 above and adjacent to a generally semi-circular groove 56. Such a configuration for the chuck 28 is typically employed in the dental industry for connecting or interfacing dental tool bits to dental drills or handpieces.

In other embodiments, the mounting shank 22 and chuck 28 may be dimensioned and configured in a variety of manners with efficacy, as required or desired, giving due consideration to the goal of connecting the drilling bit 10 to a dental drilling system. The mounting shank 22 further includes a longitudinal passage 30 extending from the proximal end 28 to the linking member 26, as illustrated in FIG. 5. Preferably, the passage 30 is generally cylindrical in shape and is located substantially centrally within the mounting shank 22. The passage 30 is dimensioned and configured to accommodate the irrigation cannula 14 (FIG. 1).

Referring to FIGS. 3 to 6, the linking member 26 is generally cylindrical in shape and in mechanical communication with the mounting shank 22 and the cutting head 24. During drilling, the linking member 26 rotates along with the cutting head 24 and the mounting shank 22. The linking member 26 includes a lateral through hole 32 (FIG. 4). The hole 32 of the linking member 26 is in communication with the passage 30 of the mounting shank 22. In one embodiment, the linking member 26 is also coated with a hard carbon coating, and more preferably a diamond-like carbon (DLC) coating, as schematically illustrated by the coating 20 (FIG. 2). The coating can reduce adhesion of any bone chips or other debris to the linking member 26, and thus make it easier to clean and sterilize the drilling bit 10. The coating 20 also desirably improves the corrosion resistance of the linking member 26.

In one embodiment, the hole 32 of the linking member 26 houses an insert or plug (not shown). Preferably, the plug is fabricated from silicone. The plug includes a generally longitudinal through hole and serves to hold the irrigation cannula 14 (FIG. 1) in place and prevent undesired movement of the cannula 14 during drilling operations.

In one embodiment, and referring to FIGS. 3 to 6, the cutting head 24 generally includes a plurality of flutes defining a plurality of side cutting edges 34 and terminating in a plurality of end cutting edges 36. The side cutting edges 34 extend along the length of the cutting head 24 and terminate in the end cutting edges 36. The end cutting edges terminate to define a cutting tip or end 38 of the cutting head 24. In one embodiment, the cutting head 24 includes three side cutting edges 34. In one embodiment, the cutting head 24 includes three end cutting edges 36. In other embodiments, as the skilled artisan will recognize, the cutting head 24 can include fewer or more side cutting edges 34 and/or end cutting edges 36, as required or desired.

In one embodiment, the entire cutting head 24 is coated with a hard carbon coating and more preferably with a diamond-like carbon (DLC) coating 20, as schematically illustrated by the coating 20 (FIG. 2). For example, the coating 20 may be formed by a physical vapor deposition (PVD) and/or chemical vapor deposition (CVD) technique, though other coating techniques may be utilized with efficacy, as required or desired, giving due consideration to the goal of providing a hard carbon coated dental cutting tool with improved performance.

Referring again to FIGS. 3 to 6, the cutting head 24 further includes a longitudinal passage 40 in fluid communication with a plurality of openings 42 proximate to the cutting head tip 38. The passage 40 is also in communication with the hole 32 (FIG. 4) of the linking member 26. Preferably, the passage 40 is generally cylindrical in shape and is located substantially centrally within the cutting head 24 in general alignment with the passage 30. The passage 40 is dimensioned and configured to accommodate the irrigation cannula 14 (FIG. 1). During drilling operations, the irrigation cannula 14 extends through the mounting shank passage 30, linking member hole 32 and into the cutting head passage 40, thereby rendering the irrigation cannula 14 in fluid communication with the cutting head openings 42. Thus, the irrigation cannula 14 can provide fluid during drilling operations to wash away bone debris/chips (and tissue) and to cool the drilling bit 10. Typically, a saline solution or sterile water is used as the irrigation fluid.

In one embodiment, the cutting head 24 (FIGS. 3 and 4) includes three openings 42. In other embodiments, as the skilled artisan will recognize, the cutting head 24 can include fewer or more openings 42, as required or desired.

Referring to FIGS. 3 and 4, in one embodiment, the cutting head 24 includes a plurality of depth indicating indicators, such as bands 44. As discussed in greater detail later herein, the bands 44 are a visual indicator of the depth of bone penetration and are preferably distinguishable in color from the remainder of the outer surface of the cutting head 24. The bands 44 can fully or partially circumscribe the perimeter of the cutting head 24. In one embodiment, the cutting head 24 includes four depth indicating bands 44. In other embodiments, the cutting head 24 may include fewer or more bands 44, as required or desired, giving due consideration to the goal of providing generally reliable depth indicating means, and/or of achieving one or more of the benefits as taught or suggested herein.

Referring in particular to FIGS. 3 and 4, in one embodiment, the drilling bit 10 has a length of about 38.1 mm (1.50 inches). In one embodiment, the mounting shank 22 has a length of about 14.5 mm (0.57 inches), the cutting head 24 has a length of about 20.6 mm (0.81 inches), and the linking member 26 has a length of about 3.0 mm (0.12 inches). In other embodiments, the drilling bit 10 may be dimensioned and configured in a wide variety of manners, as required or desired, depending on the particular nature of the osteotomy to be formed.

In one embodiment, and referring to FIGS. 3 to 6, the cutting head 24 is dimensioned and configured to provide a cutting or osteotomy diameter of about 3.8 mm (0.15 inches). In another embodiment, the cutting head 24 is dimensioned and configured to provide a cutting or osteotomy diameter in the range from about 1.5 mm (0.06 inches) to about 6.0 mm (0.24 inches). In one embodiment, the cutting head 24 is dimensioned to form an osteotomy having sufficient depth to house dental implants (not shown) with lengths ranging from about 8 mm (0.31 inches) to about 18 mm (0.71 inches). In other embodiments, the cutting head 24 may be dimensioned and configured in a wide variety of manners, as required or desired, depending on the particular nature of the osteotomy to be formed and the implant to be used.

The depth indicating bands 44 (FIGS. 3 and 4) generally have a width within the range of from about 0.5 mm (0.02 inches) to about 1.5 mm (0.06 inches), and, in one embodiment about 0.76 mm (0.03 inches). In other embodiments, the bands 44 may be dimensioned and configured in a wide variety of manners, as required or desired, giving due consideration to the goal of providing generally reliable and durable depth indicating means, and/or of achieving one or more of the benefits as taught or suggested herein. Alternatively, the bands 44 can be formed on one or more grooves or notches provided on the cutting head 24. These grooves can have a depth in the range from about 0.06 mm (0.0025 inches) to about 0.5 mm (0.02 inches), and, in one embodiment, about 0.13 mm (0.005 inches) to about 0.25 mm (0.01 inches), though other suitable dimensions may be efficaciously used, as needed or desired.

Preferably, the drilling bit 10 (FIGS. 3 to 6) is fabricated from stainless steel, and more preferably from UNS S45500 (ASTM-A564). In one embodiment, the drilling bit 10 is heat treated, electro-polished and passivated prior to the application of the coating 20 (FIG. 2). In other embodiments, the drilling bit 10 may be fabricated from a wide variety of materials, such as other metals, alloys, ceramics, plastics, as required or desired, giving due consideration to the goal of providing reduced friction and improved drilling efficiency, and/or of achieving one or more of the benefits as taught or suggested herein.

The drilling bit 10 (FIGS. 3 to 6) is preferably manufactured by machining and/or grinding operations. In other embodiments, the drilling bit 10 may be manufactured by casting, forging and/or molding, among other known manufacturing technologies.

As indicated above, preferably, at least a portion of the drilling bit 10 (FIGS. 3 to 6) is coated with a diamond-like carbon (DLC) coating or film 20 (FIG. 2). In one embodiment, both the cutting head 24 and the linking member 26 are coated with a diamond-like carbon (DLC) coating 20. In another embodiment, only the cutting head 24 is coated with diamond-like carbon (DLC) film 20. It is preferred that the mounting shank 22 not be coated with diamond-like carbon (DLC) to maintain good frictional grip and to reduce the creation of unwanted carbon particulate matter when the mounting shank 22 is engaged with the handpiece or drill 12 (FIG. 1). In alternative embodiments, some or all of the mounting shank 22 may be coated with diamond-like carbon (DLC), as required or desired. In one embodiment, the chuck 28 of the mounting shank 22 is coated with diamond-like carbon (DLC). Advantageously, the reduced friction provided by the coating 20 on the chuck 28 facilitates in the insertion/removal of the drilling bit 10 into/from the handpiece 12.

In general, a hard carbon coating or film, such as the diamond-like carbon (DLC) coating 20 (FIG. 2), may be applied to selected surfaces of the tool bit 10 (FIG. 1) in a wide variety of configurations, as required or desired, giving due consideration to the goal of reducing friction and improving performance. As indicated above, preferably, the coating 20 is formed by a physical vapor deposition (PVD) and/or chemical vapor deposition (CVD) technique, though other coating techniques may be utilized with efficacy, as required or desired, giving due consideration to the goal of providing a hard carbon coated dental cutting tool with improved performance.

In one embodiment, and referring to FIG. 2, the hard carbon coating 20 has a thickness of about 1 micron ($\mu$m). In another embodiment, the hard carbon coating 20 has a thickness in the range from about 0.5 microns ($\mu$m) to about 2.0 microns ($\mu$m). In a further embodiment, the hard carbon coating 20 has a thickness in the range from about 0.5 microns ($\mu$m) to about 100 microns ($\mu$m). In other embodiments, the thickness of the hard carbon coating 20 may be selected, as required or desired, giving due consideration to the goals of providing reduced friction and improved drilling/cutting efficiency.

As indicated above, the hard carbon coating 20 (FIG. 2) comprises at least some, and preferably, a major or substantially sizable proportion of $sp^3$ chemical bonding. In one embodiment, the hard carbon coating 20 comprises between about 70% to about 100% $sp^3$ bonding. In other embodiments, the coating 20 can comprise less $sp^3$ bonding, as required or desired, giving due consideration to achieving one or more of the benefits and advantages as taught or suggested herein.

Also, as indicated above, the hard carbon coating 20 (FIG. 2) in one embodiment comprises diamond-like carbon (DLC) which includes some hydrogenation. In one embodiment, the hydrogen content of the hard carbon or DLC coating 20 is between about 5 to about 35 atomic %. In other embodiments, the hydrogen content can be less or more, as required or desired, giving due consideration to achieving one or more of the benefits and advantages as taught or suggested herein.

In general, the present invention can be used to adjust some of the properties of the hard carbon coating 20 (FIG. 2) by varying the relative proportions of $sp^3$ and $sp^2$ bonding, and the hydrogen content. These properties can include the friction coefficient, mechanical hardness, corrosion resistance, chemical inertness, and thermal conductivity among others. In this manner, by "tweaking" the bonding and/or chemical structure of the hard carbon coating 20, it may be possible to customize the coating 20 to optimally adapt to a particular dental or other surgical application by providing a synergistic balance between one or more desirable properties of the hard carbon coating 20.

In one embodiment, the hard carbon coating 20 (FIG. 2) has a coefficient of friction of about 0.1. In another embodiment, the hard carbon coating 20 has a coefficient of friction in the range from about 0.01 to about 0.1. In other embodiments, the hard carbon coating can have a lower or higher coefficient of friction, as needed or desired, giving due consideration to the goal of achieving one or more of the benefits and advantages taught or suggested herein.

In one embodiment, the hard carbon coating 20 (FIG. 2) has a Knoop hardness of about 2000 kg/mm$^2$. In other embodiments, the hard carbon coating 20 can have a lower or higher hardness, as needed or desired, giving due consideration to the goal of achieving one or more of the benefits and advantages taught or suggested herein.

As indicated above, the hard carbon coating 20 (FIG. 2) can comprise a wide variety of commercially available "hard carbon" coatings including, but not being limited to, diamond-like carbon (DLC), amorphous diamond, crystalline diamond, or a combination thereof. For example, if the inclusion of a certain proportion of crystalline structure is advantageous for a particular dental application, the coating 20 may include a certain quantity of crystalline diamond along with diamond-like carbon (DLC) and/or amorphous diamond. Also, the coating 20 may be doped with small quantities of other materials to achieve a desired synergistic balance of the desirable properties of hard carbon coatings and given the goal of providing improved dental or surgical cutting tools, particularly for use in the field of dental implantology as related to the preparation of an osteotomy in a patient's jawbone.

The hard carbon coating 20 (FIG. 2) can be formed by a variety of techniques, for example, physical vapor deposition (PVD) processes and chemical vapor deposition (CVD) processes. The physical vapor deposition (PVD) may comprise single-ion beam sputtering, dual ion-beam sputtering, and radio-frequency (RF) sputtering, among others. The chemical vapor deposition (CVD) may include hot-filament CVD, plasma-assisted CVD (PACVD), direct-current (DC) PACVD, radio-frequency (RF) PACVD, direct-current (DC) thermal plasma (CVD), radio-frequency (RF) thermal plasma CVD, and flame CVD, among others.

It is desirable to clean the surface of the tool bit 10 (FIG. 1) prior to applying the coating 20 (FIG. 2). This facilitates better adherence of the hard carbon coating 20 to the passivated surface of the tool bit 10. Preferably, this cleaning process utilizes ultrasonic cleaning followed by a plasma cleaning of the tool bit 10. The plasma cleaning step includes bombardment of the tool bit 10 by suitable ions, such as argon ions. In one embodiment, a combination of physical vapor deposition (PVD) and chemical vapor deposition (CVD) techniques is used to form the hard carbon coating 20 (FIG. 2) on the tool bit 10 (FIG. 1). The cleaning process and application of the coating can be performed by any one of a number of commercial coating providers.

A tool bit having features and advantages of the present invention is not limited to the particular drilling bit 10, shown in FIGS. 3 to 6, but can include a wide variety of other tool bits, such as twist drilling bits, pilot drilling bits, guide drilling bits, depth drilling bits, tapered drilling bits, among other dental drilling bits as utilized in the art, giving due consideration to the goal of reducing friction and improving drilling/cutting efficiency. As discussed in greater detail later herein, in one embodiment, the tool bit comprises a cutting tip of an osteotome. The tool bit of the present invention can also comprise a root canal file as utilized in the art.

Figures 7, 8:
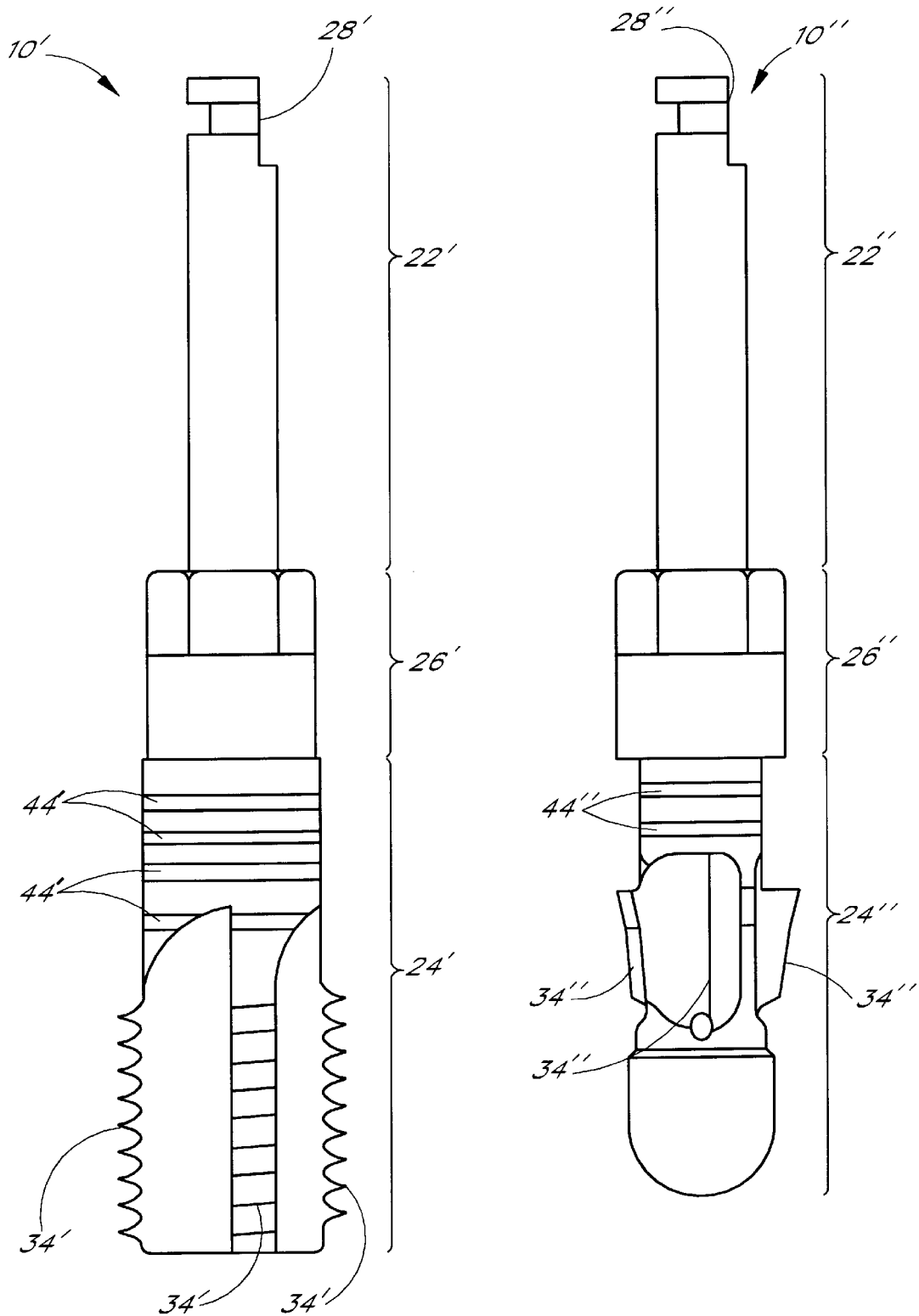
FIG. 7 is a front elevation view of a threadformer comprising depth indicating bands in accordance with one embodiment of the present invention.
FIG. 8 is a front elevation view of a counterbore comprising depth indicating bands in accordance with one embodiment of the present invention.

Additionally, in one embodiment, the tool bit 10 (FIGS. 1 and 2) is a hard carbon coated dental threadformer or tapping bit 10', as illustrated in FIG. 7, for threading an osteotomy. The general use and structure of dental threadformers is known in the art. The general construction of the threadformer 10' (FIG. 7) is similar to that of the drilling bit 10 (FIGS. 3 and 4) except that the cutting/threading head 24' of the threadformer 10' is adapted to thread an osteotomy and includes cutting/threading edges 34'. Preferably, the cutting/threading head 24' of the threadformer 10' includes the hard carbon coating 20 (FIG. 2), though other portions (for example, the linking member 26' and/or the mounting shank 22') can include it also, as required or desired, giving due consideration to the goal of achieving one or more of the benefits and advantages of the present invention, such as providing reduced friction and improved performance, among other benefits and advantages. The hard carbon coating 20 (FIG. 2) in one embodiment comprises diamond-like carbon (DLC), and in another embodiment it includes amorphous diamond. In other embodiments, the coating 20 can comprise crystalline diamond, or a combination of two or more of diamond-like carbon (DLC), amorphous diamond, and crystalline diamond. In one embodiment, the cutting head 24' of the threadformer 10' (FIG. 7) includes depth indicating bands 44' (FIG. 7) which are similar to the depth indicating bands 44.

In one embodiment, the tool bit 10 (FIGS. 1 and 2) is a hard carbon coated dental counterbore or countersink 10", as illustrated in FIG. 8, for countersinking an osteotomy. The general use and structure of dental counterbores is known in the art. The general construction of the counterbore 10" (FIG. 8) is similar to that of the drilling bit 10 (FIGS. 3 and 4) except that the cutting/counterboring head 24" of the counterbore 10" is adapted to counterbore an osteotomy and includes cutting/counterboring edges or flutes 34". Preferably, the cutting/counterboring head 24" of the counterbore 10" includes the hard carbon coating 20 (FIG. 2), though other portions (for example, the linking member 26" and/or the mounting shank 22") can include it also, as required or desired, giving due consideration to the goal of achieving one or more of the benefits and advantages of the present invention, such as providing reduced friction and improved performance, among other benefits and advantages. The hard carbon coating 20 (FIG. 2) in one embodiment comprises diamond-like carbon (DLC), and in another embodiment it includes amorphous diamond. In other embodiments, the coating 20 can comprise crystalline diamond, or a combination of two or more of diamond-like carbon (DLC), amorphous diamond, and crystalline diamond. In one embodiment, the cutting head 24" of the counterbore 10" (FIG. 1) includes depth indicating bands 44" (FIG. 8) which are similar to the depth indicating bands 44.

In general, the hard carbon coating 20 (FIG. 2) of the present invention can be applied to a wide variety of osteotomy preparation dental tools and other dental or surgical tools as utilized in the art, giving due consideration to the goal of providing reduced friction, enhanced cutting performance, high corrosion resistance and other benefits and advantages.

Referring to FIG. 9, in one embodiment, the coated dental instrument or tool bit of the present invention comprises a hard carbon coated cutting tip 10*a* of an osteotome or dental cutting system/apparatus 110*a*. An osteotome aids in the placement of implants in soft bony material, for example, in soft maxillary bone. Osteotomes compress the bone laterally, providing a denser bony interface, rather than removing valuable bone from the surgical site.

The dental tool, osteotome or diamotome 110*a* (FIG. 9) further comprises a handle or handpiece 12*a* in mechanical communication with the cutting tip or tool 10*a*. The handle 12*a* provides a gripping/holding surface for the dental practitioner to manually manipulate the osteotome 110*a*. The cutting tip 10*a* of the osteotome 110*a* is pressed, pushed, and/or twisted in a back and forth rotating/turning motion in the bony material to form an osteotomy. Thus, the cutting tip 10*a* axially and/or rotatingly cuts/compresses bony material. After the creation of the osteotomy, other instruments such as thread formers and counterbores, among others, may be used, as required or desired, depending on the particular nature of the osteotomy to be formed and the implant to be used.

Advantageously, the hard carbon coating 20 (FIG. 2) formed on the surface of the osteotome cutting tip 10*a* (FIG. 9) provides a low coefficient of friction between the cutting instrument 10*a* and the bony material. This improves the efficiency of the osteotomy preparation procedure and reduces the effort expended by the dental practitioner. Another benefit of the low friction (improved lubriciousness) is that it reduces the adhesion of bone/tissue and other debris to the cutting tip 10*a*. Desirably, this allows for easier cleaning and sterilization of the cutting tip 10*a* (and the osteotome 110*a*).

Referring to FIG. 9, the osteotome cutting tip 10*a* generally comprises a mounting shank 22*a* and a cutting head 24*a* joined by a linking/spacing member 26*a*. The mounting shank 22*a* includes a generally cylindrical protrusion 70 that is received in a cavity 71 of the handle 12*a* to attach the cutting tip 10*a* to the handle 12*a*. Preferably, the protrusion 70 is sized and configured to form a press fit in the cavity 71 such that a flange 72 of the mounting shank 22*a* is seated flush with a face 73 of the handle 12*a*. In other embodiments, the cutting tip 10*a* and the handle 12*a* can be attached in a wide variety of manners utilizing, for example, screws, adhesives, and the like. The cutting tip 10*a* and the handle 12*a* may also be formed as an integral unit.

The linking/spacing member 26*a* (FIG. 9) is generally cylindrical in shape. The linking member 26*a* links the cutting head 24*a* to the mounting shank 22*a*. The spacing member 26*a* also spaces the cutting head 24*a* from the handle 12*a* by a predetermined distance, as required or desired.

In one embodiment, and referring to FIGS. 9 and 10, the cutting head 24*a* is generally cylindrical in shape and includes a distal end 74 with a flared side cutting surface 34*a* and a flared end cutting surface 36*a*. The flared side cutting surface 34*a* is generally frustoconical in shape and the flared end cutting surface 36*a* is generally conical in shape. In other embodiments, fewer or more cutting surfaces and alternatively shaped cutting surfaces may be utilized efficaciously, as required or desired, giving due consideration to the goal of improving cutting performance.

In general, a hard carbon coating or film may be applied to selected surfaces of the osteotome cutting tip 10*a* in a wide variety of configurations, as required or desired, giving due consideration to the goal of reducing friction and improving performance. Preferably, the cutting head 24*a* (FIG. 9) of the cutting tip 10*a* includes the hard carbon coating 20 (FIG. 2), though other portions (for example, the linking/spacing member 26*a*) can include it also, as required or desired, giving due consideration to the goal of achieving one or more of the benefits and advantages as taught or suggested herein, such as providing reduced friction, corrosion resistance and improved performance, among other benefits and advantages. The hard carbon coating 20 (FIG. 2) in one embodiment comprises diamond-like carbon (DLC), and in another embodiment it includes amorphous diamond. In other embodiments, the coating 20 can comprise crystalline diamond, or a combination of two or more of diamond-like carbon (DLC), amorphous diamond, and crystalline diamond.

As discussed above, the hard carbon coating 20 (FIG. 2) can be formed on the cutting tip 10*a* (FIG. 9) by a variety of techniques, for example, physical vapor deposition (PVD) and/or chemical vapor deposition (CVD), among others. Also, as indicated above, prior to the application of the hard carbon coating the cutting tip 10*a* is passivated and cleaned. Prior to the passivation, preferably, the linking/spacing member 26*a* is glass bead blasted to provide a satin finish.

In one embodiment the hard carbon coating/film 20 (FIG. 2) formed on the osteotome cutting tip 10*a* (FIG. 9) has a thickness of about 1 micron ($\mu$m). In another embodiment, the hard carbon coating 20 has a thickness in the range from about 0.5 microns ($\mu$m) to about 2.0 microns ($\mu$m). In a further embodiment, the hard carbon coating 20 has a thickness in the range from about 0.5 microns ($\mu$m) to about 100 microns ($\mu$m). In other embodiments, the thickness of the hard carbon coating 20 may be selected, as required or desired, giving due consideration to the goals of providing reduced friction and improved cutting efficiency and performance.

Preferably, the cutting head 24*a* (FIG. 9) includes a plurality of depth indicating bands 44*a*. The bands 44*a* are a visual indicator of the depth of bone penetration and are preferably distinguishable in color from the remainder of the outer surface of the cutting head 24*a*. The bands 44*a* can fully or partially circumscribe the perimeter of the cutting head 24*a*. In one embodiment, the cutting head 24*a* includes seven depth indicating bands 44*a*. In other embodiments, the cutting head 24*a* may include fewer or more bands 44*a*, as required or desired, giving due consideration to the goal of providing generally reliable depth indicating means, and/or of achieving one or more of the benefits and advantages as taught or suggested herein.

Referring to FIG. 9, in one embodiment, the osteotome 110*a* has an overall length of about 165 mm (6.5 inches) and a major diameter of about 14.7 mm (0.58 inches). In other embodiments, the osteotome 110*a* may be dimensioned and configured in a wide variety of manners, as required or desired, depending on the particular nature of the osteotomy to be formed.

In one embodiment, the osteotome cutting tip 10*a* (FIG. 9) has a length of about 88.9 mm (3.50 inches). In one embodiment, the mounting shank 22a has a length of about 14.2 mm (0.56 inches), the cutting head 24a has a length of about 25.4 mm (1.00 inches), and the linking/spacing member 26a has a length of about 49.3 mm (1.94 inches). In other embodiments, the cutting tip 10a may be dimensioned and configured in a wide variety of manners, as required or desired, depending on the particular nature of the osteotomy to be formed.

Referring to FIG. 9, in one embodiment, the osteotome cutting head 24a is dimensioned and configured to provide a cutting or osteotomy diameter in the range from about 1.5 mm (0.06 inches) to about 6.0 mm (0.24 inches). In one embodiment, the cutting head 24a is dimensioned to form an osteotomy having sufficient depth to house dental implants (not shown) with lengths ranging from about 8 mm (0.31 inches) to about 18 mm (0.71 inches). In other embodiments, the cutting head 24a may be dimensioned and configured in a wide variety of manners, as required or desired, depending on the particular nature of the osteotomy to be formed and the implant to be used.

In one embodiment, the osteotome handle 12a (FIG. 9) has an overall length of about 88.9 mm (3.5 inches) and a major diameter of about 14.7 mm (0.58 inches). In other embodiments, the handle 12a may be dimensioned and configured in a wide variety of manners, as required or desired, giving due consideration to the goal of providing reliable and convenient means for manipulating the osteotome.

The depth indicating bands 44a (FIG. 9) have a width within the range of from about 0.13 mm (0.005 inches) to about 0.5 mm (0.02 inches), and in one embodiment, about 0.25 mm (0.01 inches). In other embodiments, the bands 44a may be dimensioned and configured in a wide variety of manners, as required or desired, giving due consideration to the goal of providing generally reliable and durable depth indicating means, and/or of achieving one or more of the benefits and advantages as taught or suggested herein. Alternatively, the bands 44a can be formed on one or more grooves or notches provided on the cutting head 24a. These grooves can have a depth in the range from about 0.04 mm (0.0015 inches) to about 0.3 mm (0.012 inches), and, in one embodiment, about 0.08 mm (0.003 inches) to about 0.15 mm (0.006 inches), though other suitable dimensions may be efficaciously used, as needed or desired.

Preferably, the osteotome cutting tip 10a (FIG. 9) is fabricated from a titanium alloy, and more preferably from Ti-6Al-4V (UNS R56400—AMS4928N or AMS4967G). In other embodiments, the cutting tip 10a may be fabricated from a wide variety of materials, such as other metals, alloys, ceramics, plastics, as required or desired, giving due consideration to the goal of providing improved cutting performance.

Preferably, the osteotome handle 12a (FIG. 9) is fabricated from a titanium alloy, and more preferably from Ti-6Al-4V (UNS R56400—AMS4928N or AMS4967G). In one embodiment, the handle 12a is glass bead blasted to provide a satin finish, passivated and then anodized. In other embodiments, the handle 12a may be fabricated from a wide variety of materials, such as other metals, alloys, ceramics, plastics, as required or desired, giving due consideration to the goal of providing convenient gripping/holding means.

The osteotome 110a (FIG. 9) is preferably manufactured by machining and/or grinding operations. In other embodiments, the osteotome 110a may be manufactured by casting, forging and/or molding, among other known manufacturing technologies.

The hard carbon coated tool bit or dental instrument of the present invention demonstrates certain advantages over conventional dental tool bits. As indicated above, the hard carbon coating 20 (FIG. 2) can be a diamond-like carbon (DLC) coating, an amorphous diamond coating, a crystalline diamond coating, or a combination thereof. In one embodiment, the coating 20 comprises diamond-like carbon (DLC). In another embodiment, the coating comprises amorphous diamond. The present invention exploits some or all of the desirable properties of hard carbon to provide improved dental cutting tools particularly adapted to the field of dental implantology as relating to forming an osteotomy in the jawbone of a patient.

One advantage of the coating 20 (FIG. 2) is that it provides a reduced coefficient of friction (or improved lubriciousness) between the coated tool bit and the bone material and desirably increases the cutting efficiency of the tool bit(s). The reduced friction decreases the risk of bone fracture and tool bit breakage, and has several other beneficial effects. The enhanced cutting efficiency can reduce the drilling/cutting time, and thereby result in less surgery time for the patient. This not only reduces the physical discomfort of the patient, but can also reduce the monetary expense associated with the surgical procedure.

The reduced friction (improved lubriciousness) also results in less heat generation during drilling. This decreases the chances of bone "necrosis" due to burning. Another beneficial effect of the reduced friction is that it can lessen the pain and shock involved with the penetration of the dental tool bit(s) in the patient's jawbone. Also, the improved lubriciousness can reduce the rotational torque between the tool bit and the bony material. This further reduces the risk of bone fracture and tool bit breakage, and hence shields the patient from undue pain and trauma.

Also, the reduced friction (enhanced lubriciousness) permits less axial thrust and/or rotational force to be applied by the operator during drilling/cutting. This facilitates an easier osteotomy preparation process for the operator. The decrease in frictional forces between the hard carbon coated dental instrument and the bony material can also increase the operational lifetime of the instrument, and hence decrease cost.

Another benefit of the reduced friction (improved lubriciousness) as provided by the coating 20 (FIG. 2) is that it reduces the adhesion of tissue/bone to the tool bit of the present invention. Desirably, this allows for easier cleaning of the soiled tool bit(s) following a surgical procedure. Also, in the case of threadformers (tapping bits) 10' (FIG. 7), the low friction provided by the coating 20 reduces the chances of the threadformer 10' getting stuck in the osteotomy.

Advantageously, the amorphous hard carbon coating 20 (FIG. 2) provides a mechanical barrier which prevents the release of heavy metals from the stainless steel material forming the tool bit or dental instrument. It is known that stainless steel is a highly thrombogenic material because it releases chromium and nickel which can destroy enzymes and/or proteins. Also, another benefit of the coating 20 is that it exhibits minimal adhesion to proteins, and hence makes the tool bit easier to clean.

The reduced friction as provided by the coating 20 (FIG. 2) may also allow drilling, counterboring and threading speeds (RPM) that are higher than those permitted with conventional dental tool bits. Advantageously, this can make the osteotomy preparation time faster, and hence reduce the duration of the surgical procedure.

Another advantage of the coating 20 (FIG. 2) is that it has a high thermal conductivity, and hence dissipates heat at a fast rate during the drilling/cutting procedure. This better heat transfer reduces heat build-up and reduces the chances of bone "necrosis" due to burning.

Another advantage of the coating 20 (FIG. 2) is that it provides increased surface hardness to the tool bit and improves its wear resistance properties and durability. This increases the lifetime of the tool bit cutting edges, for example, the side cutting edges 34 (FIGS. 3 and 4) and the end cutting edges 36 (FIGS. 3 and 4), and hence reduces frequent replacement of the tool bit, and thus reduces cost.

Another advantage of the coating 20 (FIG. 2) is that it provides a high degree of corrosion resistance. The coated dental instrument is exposed to a corrosive environment in the patient's mouth and also during sterilization, for example, by autoclaving, dry heating or chemclaving. The coating 20 increases the lifetime and durability of the instrument, and hence reduces frequent replacement, and thus reduces cost.

Another advantage of the coating 20 (FIG. 2) is that it is chemically inert and biocompatible. This permits the tool bit to be safely used in surgical procedures involved in the preparation of an osteotomy in a patient's jawbone and the like

Pseudo-Etching of Coated Surgical Instruments

Figure 11A:
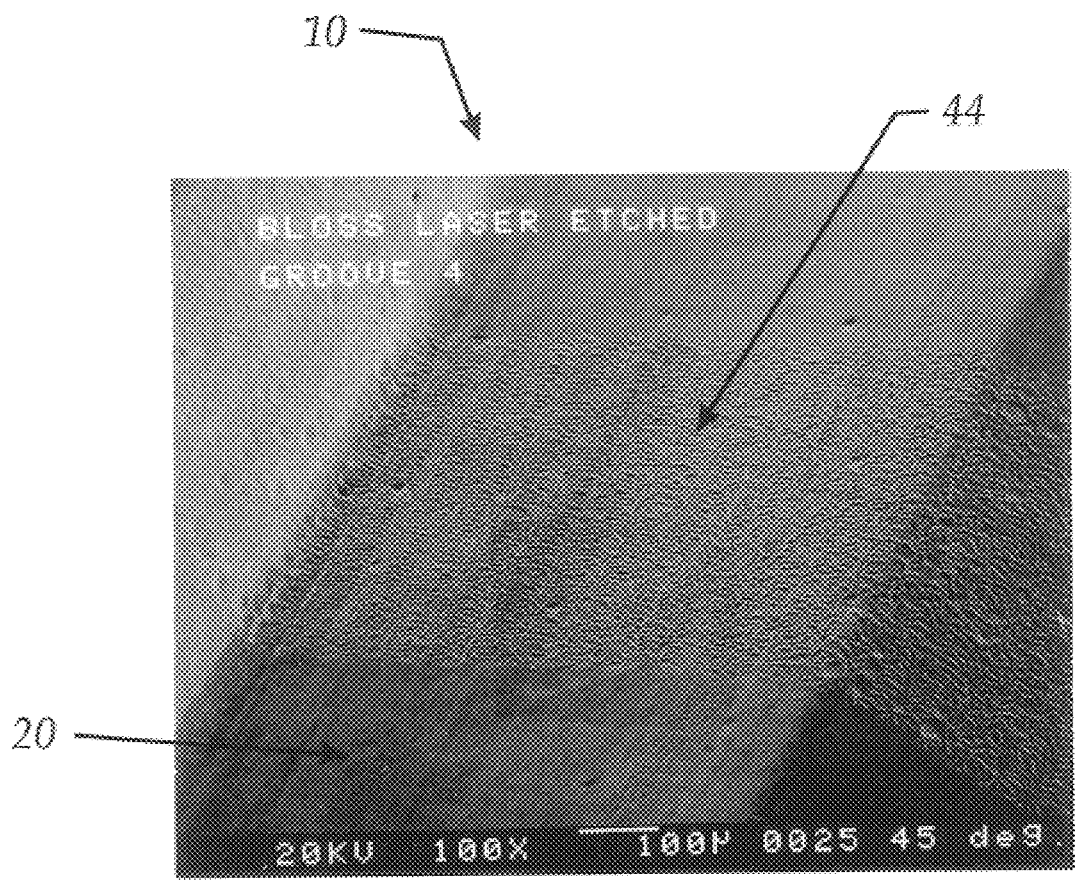
FIGS. 11A and 11B are scanning electron microscopy (SEM) photographic illustrations of depth indicating bands formed on a tool bit in accordance with one embodiment of the present invention.
Figure 11B:
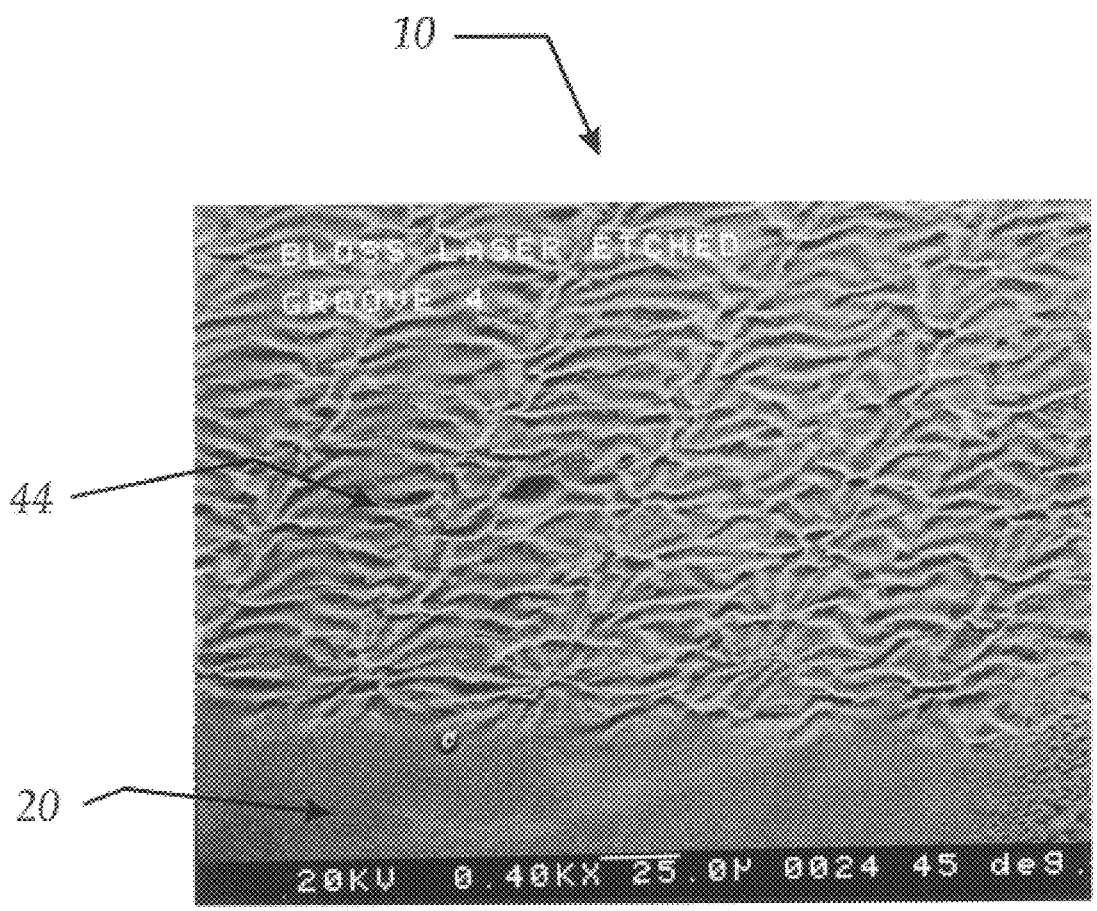

FIGS. 11A and 11B, in accordance with one embodiment, show scanning electron microscopy (SEM) photographic illustrations of depth indicating bands 44 formed on the hard carbon coated tool bit or surgical instrument 10 to provide a reliable and durable depth gauging or marking system. As indicated above, the pseudo-etched depth indicating bands, indicia or markings can be provided on instruments including but not limited to dental drilling bits 10 (FIGS. 3–6), dental threadformers or tapping bits 10' (FIG. 7), dental counterbores or countersinks 10" (FIG. 8), the cutting tips of osteotomes 10a (FIGS. 9–10) used in soft bony material, dental measuring probes or instruments for checking the depth of an osteotomy, and the like.

The depth gauging system can also be provided in conjunction with twist drilling bits, pilot drilling bits, guide drilling bits, depth drilling bits, tapered drilling bits, among other drilling bits as utilized in the art. The depth indicating bands can further be provided on a root canal file and other surgical instruments. For clarity and brevity of disclosure, the following discussion refers to the tool bit 10 and bands 44, though it should be understood that the description is applicable to any or all of the embodiments taught or suggested herein, for example, the instruments 10', 10", 10a with bands 44', 44", 44a, among others.

Preferably, the depth indicating bands and/or other markings or indicia 44 on the coated tool bit 10 are formed by pseudo-etching or processing with high intensity light to provide visual differentiation. Suitable high intensity collimated light may be generated by a laser, in one example, used in an industrial laser melting technique. Optionally, other suitable energy or heat sources, or chemical or mechanical etching techniques or means may be utilized giving due consideration to the goals of providing a surface treatment that does not adversely affect the bulk properties of the coated tool bit 10, and particularly the protective coating properties of the amorphous hard carbon, such as the corrosion resistance among other properties.

A Nd-YAG laser may be used to pseudo-etch or form the depth indicating bands 44 on the tool bit 10 selectively coated with the hard carbon film 20. Alternate suitable lasers or energy sources can also be efficaciously used, as required or desired, giving due consideration to the goals of achieving one or more of the advantages and benefits as taught or suggested herein.

In one embodiment, the laser is operated at a voltage in the range from about 24.5 Volts to about 24.9 Volts. In alternate embodiments, other operating voltages may be efficaciously employed, as required or desired, giving due consideration to the goals of achieving one or more of the advantages and benefits as taught or suggested herein. Generally, lasers with continuous outputs between about 0.5 kW to about 10 kW can be used to form the depth indicating bands 44 on the coated tool bit 10.

In one embodiment, the laser pseudo-etching comprises a melting process with or without mixing of the precoated hard carbon 20 with the underlying material (substrate) forming the tool bit 10. This is preferably followed by rapid melt quenching.

In one embodiment, the surface modification to form the laser pseudo-etched/processed depth indicating bands 44 on the coated tool bit 10 is caused by surface melting processes. Alternatively, or in addition, the surface modification is caused by transformation hardening, in which the surface is heated so that thermal diffusion and solid-state transformations can take place. In one embodiment, a rapid quenching from the melt is performed, which results in refinement of the structure of the pseudo-etched bands 44.

In one embodiment, the structure of the surface layer forming the depth indicating bands or indicia 44 results from the heating and melting only of the underlying material (substrate) forming the tool bit 10. In one embodiment, a rapid melt quenching is also performed. This treatment of the underlying tool bit material (substrate) alters the reflectance of the overlying hard carbon coating 20, and hence that of the laser pseudo-etched regions or bands 44 of the tool bit 10, by modifying the surface texture. Thus, visual differentiation is provided between the bands 44 and the hard carbon coating 20. In this embodiment, there is substantially no mixing between the underlying tool bit material (substrate) and the hard carbon coating 20.

In one embodiment, the structure of the surface layer forming the depth indicating bands or indicia 44 results due to a chemical alteration. The bands 44 comprise a mixture of the underlying material (substrate) forming the tool bit 10 with trapped particles of hard carbon. In this embodiment, the laser pseudo-etching heats and melts the underlying material of the tool bit 10 and/or the hard carbon coating 20 and forms a mixture comprising the two which has a color and/or contrast different from that of the hard carbon coating 20. In one embodiment, a rapid melt quenching is also performed.

In one embodiment, the structure of the surface layer forming the depth indicating bands or indicia 44 is a combination of the alteration in reflectance of the overlying hard carbon coating 20 due to treatment of the underlying tool bit material (substrate) and a chemical alteration due to the formation of mixture of the underlying material (substrate) of the tool bit 10 and the hard carbon forming the coating 20.

In one embodiment, the use of a laser beam to form the bands 44 has the advantage that the boundary lines between the bands 44 and adjacent surfaces of the tool bit 10 are sharp and well defined. Thus, the contrast or transition between colors will be high, thereby providing sharp visual differentiation.

In one embodiment, the bands 44 are substantially white or light gray in color compared to the hard carbon coating 20 which is substantially black or dark gray in color. Preferably, the underlying material forming the tool bit or instrument 10 comprises stainless steel and, more preferably, UNS S45500 (ASTM-A564). Alternatively, the underlying material forming the tool bit or instrument 10 can comprise titanium or a titanium alloy such as Ti-6Al-4V (UNS R56400—AMS4928N or AMS4967G). In other embodiments, the underlying material forming the tool bit or instrument 10 can comprise other metal, alloys or other suitable materials, as needed or desired, giving due consideration to the goals of providing visual differentiation, and/or of achieving one or more of the benefits and advantages as taught or suggested herein.

As indicated above, in one embodiment, the bands 44 are substantially white or light gray in color compared to the hard carbon coating 20 which is substantially black or dark gray in color. Other color differentiations are also within the scope of the invention. Advantageously, the laser processing/pseudo-etching modifies the surface structure of the hard carbon coated tool 10 without adversely affecting the bulk and/or surface properties of the hard carbon coating 20. The result is that the substantially white or light gray depth indicating bands 44, though quite different in color from the substantially black or dark gray hard carbon background, substantially retain the desirable properties of hard carbon, and particularly the protective coating properties, such as the corrosion resistance and the like. The laser processing may also be utilized to tailor the surface properties of the hard carbon coated tool bit 10.

In one embodiment, the laser pseudo-etching or processing is controlled to a depth which is substantially the same, slightly smaller or slightly greater than the thickness of the hard carbon layer or film 20 on the dental tool bit or instrument 10. In other embodiments, the depth of the laser pseudo-etching can be alternately selected, as required or desired, giving due consideration to the goals of achieving one or more of the advantages and benefits as taught or suggested herein.

In one embodiment, the depth indicating bands 44 are annular or circumferential in shape and circumscribe the outer surface of the cutting head 24. Each band 44 can form a continuous band or comprise a number of discrete band elements, as required or desired, giving due consideration to the goals of achieving one or more of the advantages and benefits as taught or suggested herein. The bands 44 may also only partially circumscribe the outer surface of the cutting head 24, as required or desired, giving due consideration to the goals of achieving one or more of the advantages and benefits as taught or suggested herein.

If desired, circumferential grooves or notches, which correspond to the location of respective depth indicating bands 44, may be formed on the tool bit 10 prior to the application of the hard carbon coating 20. After the application of the hard carbon coating 20, laser processing or pseudo-etching can be used to provide the depth indicating bands having features in accordance with the present invention.

The depth indicating bands 44 are located at predetermined distances from one another and have a predetermined width. The locations of the depth indicating bands 44 typically correspond to the particular length of the dental implant that is to be fixtured in the osteotomy. The bands can also be spaced to take into account the length of a healing screw that would cap the implant during an initial healing period. In this context, the width of the bands 44 can be used to provide a double depth measurement, for example, the lower edge of the band 44 would indicate the absolute length of the implant while the upper edge of the band 44 would correspond to the distance the healing screw would protrude above the implant.

The tool bit 10 can comprise one or more depth indicating bands 44. In one embodiment, the tool bit 10 comprises four depth indicating bands 44. In another embodiment, the tool bit 10 comprises between two and eight depth indicating bands 44. Each depth indicating band 44 has a width in the range of from about 0.5 mm (0.02 inches) to about 1.5 mm (0.06 inches), and, in one embodiment, a width of about 0.76 mm (0.03 inches). The center-to-center spacing between adjacent bands 44 is in the range of from about 1 mm (0.04 inches) to about 4 mm (0.16 inches), and, in one embodiment, about 2.03 mm (0.08 inches). In other embodiments, the depth indicating bands 44 can be configured and/or dimensioned in a wide variety of manners with efficacy, as required or desired, giving due consideration to the goals of achieving one or more of the advantages and benefits as taught or suggested herein. Also, the laser processing can result in the osteotomy depth indicating bands 44 being slightly recessed relative to the adjacent hard carbon coated surface of the tool bit 10. In other words, the laser processing can create depth indicating bands comprising a grooved structure.

The skilled artisan will readily recognize the utility of the present invention. The laser processing technique to pseudo-etch the depth indicating bands 44 on the hard carbon coated dental tool bit or instrument 10 results in a surface structure that advantageously does not have an adverse affect on and substantially preserves or retains some or all of the bulk properties of the hard carbon coating 20 applied to selected surfaces of the dental tool bit 10. As indicated above these protective properties of the amorphous hard carbon coating include corrosion resistance, biocompatibility and chemical inertness. Other desirable properties of the amorphous hard carbon coating include a low coefficient of friction, high mechanical hardness and high thermal conductivity.

Consequently, the formation of the depth indicating bands 44 on the hard carbon coated dental tool bit 10 does not substantially adversely affect the performance of the tool bit. Moreover, and advantageously, the high degree of corrosion resistance preserved by the surface of the depth indicating bands 44 does not require frequent replacement, repair and/or maintenance of the tool bit 10. This desirably translates into low cost.

Operation

In operation, the dental drilling system 110 (FIG. 1), including the tool bit 10 with the coating 20 and the bands 44, the handpiece 12 and the irrigation cannula 14, is used in the preparation of one or more osteotomies in a patient's jawbone. The motorized handpiece 12 is held in the operator's hand and the tool bit 10 is positioned at the desired osteotomy site. The handpiece 12 provides rotational motion to the tool bit 10 for penetrating the patient's jawbone. The procedure can involve the use of one or more types of tool bits 10, such as twist drilling bits, pilot drilling bits, guide drilling bits, depth drilling bits, tapered drilling bits, among other dental drilling bits as utilized in the art. Typically, the procedure involves using tool bits 10 of progressively increasing size to gradually increase the size of the osteotomy. In the latter stages, depth drilling bits, such as the drilling bit 10 (FIGS. 3 and 4) with depth indicating bands 44 are utilized to finalize the size and depth of the osteotomy as predetermined or dictated by the particular implant and/or healing screw selected by the dental surgeon.

During drilling the irrigation cannula 14 is used to provide fluid (typically saline solution or sterile water) to the drilling site. Typically, when drilling, an in-and-out-motion is utilized with the drilling bit 10 being periodically withdrawn from the bone to allow the irrigation fluid to wash away bone chips/debris (and tissue). The irrigation also assists in cooling the tool bit 10 and the osteotomy site. One or more osteotomies may be prepared in this manner, as dictated by the particular needs of the patient. Because of the reduced coefficient of friction, the hard carbon coated dental instrument exhibits a reduced adhesion tendency for soft tissue, thereby rendering the instrument easier to clean. The depth indicating bands 44 allow the surgeon to precisely, exactly and accurately control the size/depth of the osteotomy to ensure that the implant is properly seated therein.

In some cases, after the drilling bits 10 (FIGS. 3 and 4) have been used to form an osteotomy, a counterbore 10" (FIG. 8) with bands 44" is utilized to countersink the osteotomy to a predetermined depth. This procedure may be used to prepare the osteotomy for handling a particular type of dental implant, for example, one having a larger diameter at the gingival end. Preferably, the counterbore 10" is used with the dental drilling system 110 (FIG. 1).

The osteotomy may be used to house a cylindrical implant or a threaded implant. These implants are well known in the art, and hence will not be described herein. In the case of cylindrical implants, the implant is simply pushed into the osteotomy. Similarly, for self-tapping threaded implants, the threaded implant is threaded into the osteotomy.

In the case of non-self-tapping threaded implants, a threadformer or tapping bit 10' (FIG. 7) having bands 44' may be used to provide threads in the osteotomy to a predetermined depth. The threaded implant is then threaded into position in the threaded osteotomy. Preferably, the threadformer 10' is used with the dental drilling system 110. The threadformer 10' can also be used manually by using a ratchet, as is well known in the art.

Typically, after the preparation of the osteotomy, the tool bit(s) 10 are sterilized. As is known in the art, the sterilization procedure may utilize autoclaving, dry heating or chemclaving. Preferably, the instruments are first cleaned of all bone chips and other debris using a needle and/or a brush. Advantageously, the hard carbon coating reduces adhesion to such debris making the instruments easier to clean and sterilize. Moreover, the protective surface properties of the coating 10 and the pseudo-etched bands 44 provide safety to the patient as well as durability and longevity to the tool bit or surgical instrument 10.

While the components and techniques of the present invention have been described with a certain degree of particularity, it is manifest that many changes may be made in the specific designs, constructions and methodology hereinabove described without departing from the spirit and scope of this disclosure. It should be understood that the invention is not limited to the embodiments set forth herein for purposes of exemplification, but is to be defined only by a fair reading of the appended claims, including the full range of equivalency to which each element thereof is entitled.

What is claimed is:

1. A method of treating the surface of a surgical instrument to provide visual differentiation, comprising the steps of:
   providing said instrument comprising a cutting head and a mounting shank adapted to engage a handpiece or handle;
   forming a hard carbon coating on said cutting head of said instrument; and
   pseudo-etching one or more selected portions of the surface of said cutting head to provide one or more bands having a predetermined spacing for indicating the depth of an osteotomy, at least one of said bands comprising a mixture of hard carbon and material from said cutting head.

2. The method of claim 1, wherein said step of pseudo-etching comprises the step of laser processing.

3. The method of claim 1, wherein said step of pseudo-etching comprises the step of transformation hardening.

4. The method of claim 1, wherein said step of pseudo-etching comprises the step of surface melting.

5. The method of claim 1, wherein said instrument comprises a dental drilling bit.

6. The method of claim 1, wherein said instrument comprises a dental threadformer.

7. The method of claim 1, wherein said instrument comprises a dental countersink.

8. The method of claim 1, wherein said instrument comprises a cutting tip of an osteotome.

9. The method of claim 1, wherein said instrument comprises a dental tool bit.

10. The method of claim 1, wherein said hard carbon coating comprises diamond-like carbon (DLC).

11. The method of claim 1, wherein said hard carbon coating comprises amorphous diamond.

12. The method of claim 1, wherein said hard carbon coating comprises one or more of diamond-like carbon (DLC), amorphous diamond and crystalline diamond.

13. The method of claim 1, wherein said bands are substantially white or light gray and said hard carbon coating is substantially black or dark gray.

14. The method of claim 1, wherein said step of pseudo-etching comprises heating and melting said hard carbon and said material of said cutting head.

15. The method of claim 1, wherein said mixture has a color and/or contrast different from said hard carbon coating.

16. The method of claim 1, wherein at least one of said bands comprises hard carbon overlying treated material of said cutting head.

17. A method of processing the surface of a coated dental cutting instrument to provide visual differentiation, comprising the steps of:
   providing said instrument comprising a cutting head and a mounting shank adapted to engage a handpiece or handle, having an amorphous hard carbon film on at least said cutting head of said instrument; and
   laser processing a plurality of selected coated surfaces of said cutting head to pseudo-etch a plurality of indicia having a predetermined spacing for precisely indicating the depth of an osteotomy formed in a jawbone, at least one of said indicia comprising a mixture of amorphous hard carbon and material from said cutting head.

18. The method of claim 17, wherein said step of laser processing comprises the step of operating a Nd-YAG laser.

19. The method of claim 18, wherein said step of operating a Nd-YAG laser comprises the step of operating said laser at a voltage in the range from about 24.5 Volts to about 24.9 Volts.

20. The method of claim 17, wherein said instrument comprises a dental drilling bit.

21. The method of claim 17, wherein said instrument comprises a dental threadformer.

22. The method of claim 17, wherein said instrument comprises a dental countersink.

23. The method of claim 17, wherein said instrument comprises a cutting tip of an osteotome.

24. The method of claim 17, wherein said instrument comprises a dental tool bit.

25. The method of claim 17, wherein said amorphous hard carbon comprises diamond-like carbon (DLC).

26. The method of claim 17, wherein said amorphous hard carbon comprises amorphous diamond.

27. The method of claim 17, wherein said amorphous hard carbon comprises one or more of diamond-like carbon (DLC), amorphous diamond and crystalline diamond.

28. The method of claim 17, wherein said bands are substantially white or light gray and said amorphous hard carbon film is substantially black or dark gray.

29. The method of claim 17, wherein said instrument comprises stainless steel.

30. The method of claim 17, wherein said laser processing comprises heating and melting said amorphous hard carbon and said material of said cutting head.

31. The method of claim 17, wherein said mixture has a color and/or contrast different from said amorphous hard carbon film.

32. The method of claim 17, wherein at least one of said indicia comprises amorphous hard carbon overlying treated material of said cutting head.

33. A surgical instrument for providing visual differentiation, comprising:
   a main body portion;
   a coating of amorphous hard carbon applied on at least a portion of said main body portion;
   one or more indicia formed on said main body portion by laser pseudo-etching of selected surfaces of the hard carbon coated main body portion to provide a depth gauging system on said instrument, said indicia comprising a mixture of amorphous hard carbon and material from said main body portion; and
   whereby, the surface finish of the indicia substantially preserves the protective coating properties of amorphous hard carbon.

34. The instrument of claim 33, wherein said instrument comprises a dental drilling bit.

35. The instrument of claim 33, wherein said instrument comprises a dental threadformer.

36. The instrument of claim 33, wherein said instrument comprises a dental countersink.

37. The instrument of claim 33, wherein said instrument comprises a cutting tip of an osteotome.

38. The instrument of claim 33, wherein said instrument comprises a dental tool bit.

39. The instrument of claim 33, wherein said amorphous hard carbon comprises diamond-like carbon (DLC).

40. The instrument of claim 33, wherein said amorphous hard carbon comprises amorphous diamond.

41. The instrument of claim 33, wherein said amorphous hard carbon comprises one or more of diamond-like carbon (DLC), amorphous diamond and crystalline diamond.

42. The instrument of claim 33, wherein said indicia are substantially white or light gray and said coating of amorphous hard carbon is substantially black or dark gray.

43. The instrument of claim 33, wherein said instrument comprises stainless steel.

44. The instrument of claim 33, wherein said indicia comprise amorphous hard carbon overlying treated material of said main body portion.

45. The instrument of claim 33, in combination with a handpiece to form a dental drilling/cutting system.

46. The instrument of claim 33, wherein said mixture has a color and/or contrast different from said amorphous hard carbon.

47. A dental drilling system for preparing an osteotomy, comprising:
   a tool bit including a cutting head for removing bone/tissue material to form an osteotomy;
   a handpiece for holding said tool bit and adapted to provide rotational motion to said tool bit;
   a coating on said tool bit in the form of diamond-like carbon (DLC) for improving the cutting performance of said tool bit; and
   a plurality of pseudo-etched bands formed on said coating to provide visual differentiation and being corrosion resistant, at least one of said bands comprising a mixture of diamond-like carbon and material from said cutting head.

48. The dental drilling system of claim 47, wherein said tool bit comprises a drilling bit.

49. The dental drilling system of claim 47, wherein said tool bit comprises a tapping bit.

50. The dental drilling system of claim 47, wherein said tool bit comprises a countersink.

51. The dental drilling system of claim 47, wherein said coating has a thickness between about 0.5 $\mu$m and about 2.0 $\mu$m.

52. The dental drilling system of claim 47, further comprising an irrigation cannula for washing and/or cooling said osteotomy and said tool bit.

53. The dental drilling system of claim 47 wherein said mixture has a color and/or contrast different from said diamond-like carbon.

54. The dental drilling system of claim 47, wherein at least one of said bands comprises diamond-like carbon overlying treated material of said cutting head.

55. A method of treating the surface of a surgical instrument to provide visual differentiation, comprising the steps of:
   providing said instrument comprising a cutting head and a mounting shank adapted to engage a handpiece or handle;
   forming a hard carbon coating on said cutting head of said instrument; and
   pseudo-etching one or more selected portions of the surface of said cutting head to provide one or more bands having a predetermined spacing for indicating the depth of an osteotomy, at least one of said bands comprising hard carbon overlying treated material of said cutting head.

56. The method of claim 55, wherein said step of pseudo-etching comprises heating and melting material of said cutting head underlying said hard carbon coating.

57. The method of claim 55, wherein said step of pseudo-etching comprises altering the reflectance of said hard carbon.

58. The method of claim 55, wherein said step of pseudo-etching comprises modifying the surface texture of one or more selected portions of said cutting head.

59. The method of claim 55, wherein said step of pseudo-etching comprises laser processing.

60. The method of claim 55, wherein said step of pseudo-etching comprises transformation hardening.

61. The method of claim 55, wherein said step of pseudo-etching comprises surface melting.

62. The method of claim 55, wherein said instrument comprises a dental drilling bit.

63. The method of claim 55, wherein said instrument comprises a dental threadformer.

64. The method of claim 55, wherein said instrument comprises a dental countersink.

65. The method of claim 55, wherein said instrument comprises a cutting tip of an osteotome.

66. The method of claim 55, wherein said instrument comprises a dental tool bit.

67. The method of claim 55, wherein said hard carbon coating comprises diamond-like carbon (DLC).

68. The method of claim 55, wherein said hard carbon coating comprises amorphous diamond.

69. The method of claim 55, wherein said hard carbon coating comprises one or more of diamond-like carbon (DLC), amorphous diamond and crystalline diamond.

70. The method of claim 55, wherein said bands are substantially white or light gray and said hard carbon coating is substantially black or dark gray.

71. A method of processing the surface of a coated dental cutting instrument to provide visual differentiation, comprising the steps of:
providing said instrument comprising a cutting head and a mounting shank adapted to engage a handpiece or handle, having an amorphous hard carbon film on at least said cutting head of said instrument; and
laser processing a plurality of selected coated surfaces of said cutting head to pseudo-etch a plurality of indicia having a predetermined spacing for precisely indicating the depth of an osteotomy formed in a jawbone, at least one of said indicia comprising amorphous hard carbon overlying treated material of said cutting head.

72. The method of claim 71, wherein said step of laser processing comprises heating and melting material of said cutting head underlying said amorphous hard carbon film.

73. The method of claim 71, wherein said step of laser processing comprises altering the reflectance of said amorphous hard carbon.

74. The method of claim 71, wherein said step of laser processing comprises modifying the surface texture of one or more selected coated portions of said cutting head.

75. The method of claim 71, wherein said step of laser processing comprises operating a Nd-YAG laser.

76. The method of claim 71, wherein said instrument comprises a dental drilling bit.

77. The method of claim 71, wherein said instrument comprises a dental threadformer.

78. The method of claim 71, wherein said instrument comprises a dental countersink.

79. The method of claim 71, wherein said instrument comprises a cutting tip of an osteotome.

80. The method of claim 71, wherein said instrument comprises a dental tool

81. The method of claim 71, wherein said amorphous hard carbon comprises diamond-like carbon (DLC).

82. The method of claim 71, wherein said amorphous hard carbon comprises amorphous diamond.

83. The method of claim 71, wherein said amorphous hard carbon comprises one or more of diamond-like carbon (DLC), amorphous diamond and crystalline diamond.

84. The method of claim 71, wherein said bands are substantially white or light gray and said amorphous hard carbon film is substantially black or dark gray.

85. The method of claim 71, wherein said instrument comprises stainless steel.

86. A surgical instrument for providing visual differentiation, comprising:
a main body portion;
a coating of amorphous hard carbon applied on at least a portion of said main body portion;
one or more indicia formed on said main body portion by laser pseudo-etching of selected surfaces of the hard carbon coated main body portion to provide a depth gauging system on said instrument, said indicia comprising amorphous hard carbon overlying treated material of said main body portion; and
whereby, the surface finish of the indicia substantially preserves the protective coating properties of amorphous hard carbon.

87. The instrument of claim 86, wherein at least one of said indicia has a reflectance different from adjacent amorphous hard carbon coated surfaces of said main body portion.

88. The instrument of claim 86, wherein at least one of said indicia has a surface texture different from adjacent amorphous hard carbon coated surfaces of said main body portion.

89. The instrument of claim 86, wherein said instrument comprises a dental drilling bit.

90. The instrument of claim 86, wherein said instrument comprises a dental threadformer.

91. The instrument of claim 86, wherein said instrument comprises a dental countersink.

92. The instrument of claim 86, wherein said instrument comprises a cutting tip of an osteotome.

93. The instrument of claim 86, wherein said instrument comprises a dental tool bit.

94. The instrument of claim 86, wherein said amorphous hard carbon comprises diamond-like carbon (DLC).

95. The instrument of claim 86, wherein said amorphous hard carbon comprises amorphous diamond.

96. The instrument of claim 86, wherein said amorphous hard carbon comprises one or more of diamond-like carbon (DLC), amorphous diamond and crystalline diamond.

97. The instrument of claim 86, wherein said indicia are substantially white or light gray and said coating of amorphous hard carbon is substantially black or dark gray.

98. The instrument of claim 86, wherein said instrument comprises stainless steel.

99. The instrument of claim 86, in combination with a handpiece to form a dental drilling/cutting system.

100. A dental drilling system for preparing an osteotomy, comprising:
a tool bit including a cutting head for removing bone/tissue material to form an osteotomy;
a handpiece for holding said tool bit and adapted to provide rotational motion to said tool bit;
a coating on said tool bit in the form of diamond-like carbon (DLC) for improving the cutting performance of said tool bit; and
a plurality of pseudo-etched bands formed on said coating to provide visual differentiation and being corrosion resistant, at least one of said bands comprising diamond-like carbon overlying treated material of said cutting head.

101. The dental drilling system of claim 100, wherein at least one of said bands has a reflectance different from adjacent diamond-like carbon coated surfaces of said tool bit.

102. The instrument of claim 100, wherein at least one of said bands has a surface texture different from adjacent diamond-like carbon coated surfaces of said tool bit.

103. The dental drilling system of claim 100, wherein said tool bit comprises a drilling bit.

104. The dental drilling system of claim 100, wherein said tool bit comprises a tapping bit.

105. The dental drilling system of claim 100, wherein said tool bit comprises a countersink.

106. The dental drilling system of claim 100, wherein said coating has a thickness between about 0.5 $\mu$m and about 2.0 $\mu$m.

107. The dental drilling system of claim 100, further comprising an irrigation cannula for washing and/or cooling said osteotomy and said tool bit.

* * * * *

UNITED STATES PATENT AND TRADEMARK OFFICE
CERTIFICATE OF CORRECTION

PATENT NO.   : 6,547,562 B2
DATED        : April 15, 2003
INVENTOR(S)  : Ajay Kumar It is certified that error appears in the above-identified patent and that said Letters Patent is hereby corrected as shown below:

<u>Column 23,</u>
Line 44, "dental tool" should read -- dental tool bit. --

Signed and Sealed this

Fifteenth Day of June, 2004

JON W. DUDAS
*Acting Director of the United States Patent and Trademark Office*